United States Patent
Pan et al.

(10) Patent No.: US 10,851,146 B2
(45) Date of Patent: Dec. 1, 2020

(54) METHOD FOR PREPARING LIRAGLUTIDE INTERMEDIATE POLYPEPTIDE

(71) Applicant: AMPHASTAR NANJING PHARMACEUTICALS INC., Jiangsu (CN)

(72) Inventors: Shangshu Pan, Jiangsu (CN); Chuangen Tang, Jiangsu (CN); Cheng Li, Jiangsu (CN); Xiaorui Liu, Jiangsu (CN); Huaiyan Cui, Jiangsu (CN); Song Chen, Jiangsu (CN); Haoning Zhang, Jiangsu (CN)

(73) Assignee: AMPHASTAR NANJING PHARMACEUTICALS INC., Jiangsu (CN)

(*) Notice: Subject to any disclaimer, the term of this patent is extended or adjusted under 35 U.S.C. 154(b) by 66 days.

(21) Appl. No.: 16/502,033

(22) Filed: Jul. 3, 2019

(65) Prior Publication Data
US 2019/0359675 A1 Nov. 28, 2019

Related U.S. Application Data

(63) Continuation of application No. PCT/CN2018/116238, filed on Nov. 19, 2018.

(30) Foreign Application Priority Data

Feb. 6, 2018 (CN) .......................... 2018 1 0119330

(51) Int. Cl.
| | |
|---|---|
| *A61K 38/26* | (2006.01) |
| *A61K 38/28* | (2006.01) |
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/16* | (2006.01) |
| *A61P 3/10* | (2006.01) |
| *A61P 7/12* | (2006.01) |
| *C07K 14/605* | (2006.01) |
| *C12P 21/06* | (2006.01) |
| *C12P 21/04* | (2006.01) |
| *C12P 21/02* | (2006.01) |

(52) U.S. Cl.
CPC ............ *C07K 14/605* (2013.01); *A61K 38/26* (2013.01); *C12P 21/02* (2013.01); *C12P 21/06* (2013.01); *C07K 2319/00* (2013.01)

(58) Field of Classification Search
None
See application file for complete search history.

(56) References Cited

U.S. PATENT DOCUMENTS

2016/0159877 A1* 6/2016 Retallack ............. C07K 14/535
435/69.4

FOREIGN PATENT DOCUMENTS

| CN | 104045706 | 9/2014 | |
|---|---|---|---|
| CN | 104592381 | 5/2015 | |
| CN | 104745597 | 7/2015 | |
| CN | 106434717 | 2/2017 | |
| CN | 108191981 | 6/2018 | |
| EP | 3196206 | 7/2017 | |
| WO | WO-2014122651 A1 * | 8/2014 | ............. C07K 14/62 |

OTHER PUBLICATIONS

Nian Cheng, et al., "A novel strategy to prepare the precursor peptide of liraglutide," Process Biochemistry, vol. 62, Nov. 2017, pp. 10-15.

* cited by examiner

*Primary Examiner* — Thea D' Ambrosio
(74) *Attorney, Agent, or Firm* — JCIP Global Inc.

(57) ABSTRACT

The invention belongs to the technical field of polypeptide preparation methods, and in particular relates to a preparation method of a liraglutide intermediate polypeptide GLP-1 (7-37). In the preparation method, main steps include constructing recombinant liraglutide engineered bacteria via *E. coli* to induce expression of a liraglutide intermediate fusion protein in the form of inclusion bodies, and performing denaturation, renaturation, enzyme digestion, separation and purification to obtain the liraglutide intermediate polypeptide GLP-1 (7-37). The invention alters expression pattern into the expression of the intracellular insoluble inclusion bodies by changing a signal peptide of the recombinant sequence to increase significantly expression level. The liraglutide intermediate polypeptide prepared by the invention has a purity up to 87% or more and a yield of more than 85%.

12 Claims, 5 Drawing Sheets
Specification includes a Sequence Listing.

METHOD FOR PREPARING LIRAGLUTIDE INTERMEDIATE POLYPEPTIDE

CROSS-REFERENCE TO RELATED APPLICATION

This application is a continuation of international PCT application serial no. PCT/CN2018/116238, filed on Nov. 19, 2018, which claims the priority benefit of Chinese application no. 201810119330.0, filed on Feb. 6, 2018. The entirety of each of the above-mentioned patent applications is hereby incorporated by reference herein and made a part of this specification.

BACKGROUND

Technical Field

The invention relates to the technical field of polypeptide preparation methods, in particular to a preparation method of a liraglutide intermediate polypeptide.

Description of Related Art

Diabetes is caused by interaction of genetic and environmental factors, causing absolute or relative deficiency of insulin secretion and decreased sensitivity of target tissue cells to insulin, which will cause a series of metabolic disorders of protein, fat, water, electrolytes and so on, and among them, hyperglycemia is the main hallmark. Typical clinical cases may have manifestations such as polyuria, polydipsia, polyphagia, and weight loss, that is, symptoms of "three mores and one less". In recent years, with the improvement of the living standards, changes in dietary structure and the fact that most people move less and sit more, among other factors, the global incidence of diabetes is growing rapidly. Among them, patients with type 1 diabetes account for 10%, and patients with type 2 diabetes account for 90%.

Liraglutide is a GLP-1 analogue produced by genetic recombination technology with 97% sequence homology to human GLP-1. Unlike native GLP-1, liraglutide has pharmacokinetic and pharmacodynamic properties in humans which are more suitable for a once-a-day dosing regimen. After subcutaneous injection, it prolongs the duration of action mainly by the following mechanism: 1) slowing down the absorption by self-association; 2) binding to albumin; and 3) having higher enzyme stability to DPP-IV and NEP, so that it has a longer plasma half-life. In the patients with type 2 diabetes, it may be observed that a single administration of liraglutide increases insulin secretion rate in a glucose concentration-dependent manner. At present, liraglutide in China is completely dependent on imports and is expensive. Therefore, it is urgent to provide a preparation method of liraglutide, which will benefit to the majority of diabetic patients.

As one of representative drugs of glucagon peptide (GLP-1) analogues, liraglutide is a second-line or third-line drug to be administrated to the patients with type 2 diabetes who undergone a failure of treatment with metformin monotherapy or other antidiabetic oral drugs in the United States and Europe. The 2013 edition of CHINA GUIDELINE FOR TYPE 2 DIABETES specifies that the glucagon peptide (GLP-1) analogues are used as a third-line therapeutic drug. Several clinical trials of liraglutide have demonstrated that combination of different oral hypoglycemic agents can effectively control blood glucose, reduce body weight and systolic blood pressure of patients, and improve β islet cell function.

The structural formula of liraglutide shown in SEQ ID NO. 4 is as follows:

NH$_2$-His-Ala-Glu-Gly-Thr-Phe-Thr-Ser-Asp-Val-Ser-Ser-Tyr-Leu-Glu-Gly-Gln-Ala-Ala-Lys-(N-ε-(N-α-Palmitoyl-L-γ-glutamyl))-Glu-Phe-Ile-Ala-Trp-Leu-Val-Arg-Gly-Arg-Gly-CO OH.

From the above structural formula, it is shown that the molecular formula of liraglutide is $C_{172}H_{265}N_{43}O_{51}$ with the molecular weight of 3751.20. It is a GLP-1 derivative obtained by changing lysine (Lys) at position 34 to arginine (Arg), and adding a side chain of a 16-carbon palm fatty acid (N-ε-(γ-Glu(N-α-hexadecanoyl)) at position 26 in the native GLP-1 molecular structure.

Liraglutide was first developed by Novo Nordisk and obtained by yeast production through genetic recombination technology. Synthetic methods of an intermediate polypeptide GLP-1 (7-37) in the prior art mainly adopt chemical synthesis. For example, Patent No. CN104045706B discloses a synthetic method using a variety of large amounts of organic solvents, which is not environmentally friendly, and steps of which are cumbersome and unfavorable to large industrial scale-up. In addition, it gives rise to a number of process impurities and the total yield is only 18%.

In addition, Patent No. CN104745597A which relates to a biological preparation method discloses an expression method by intracellular soluble expression, but expression level of which is lower and is not favorable for industrialization scale-up. Patent No. CN104592381A discloses that solubilization of inclusion bodies requires a long time period, a large volume, and use of a large amount of urea. Additionally, the inclusion bodies require long-term renaturation and renatured protein concentration is only 0.2 g/L, so it needs a very large volume for the renaturation, which may be not favorable to industrial scale-up.

SUMMARY

An object of the invention is to provide a method for preparing a liraglutide intermediate polypeptide GLP-1 (7-37) by obtaining Leading Peptide-DDDDK-GLP-1 (7-37) fusion protein (SEQ ID NO: 1) through genetic recombination technology using E. coli fermentation to induce expression, and performing processes such as solubilization, denaturation, renaturation, enzyme digestion, and separation to obtain the polypeptide GLP-1 (7-37) with high yield and high purity. The method solves problems in the prior art, such as high level of impurities, low yield, the use of large amounts of reagents which are not environmentally friendly, low expression level of intracellular soluble expression, long duration of solubilization, denaturation and renaturation of inclusion bodies, and low protein concentration that leads to large volume of denaturation and renaturation, which are not suitable for large-scale production and limit the increase of production capacity.

In order to achieve the above object, the invention provides the following technical solution: a fusion protein of Leading Peptide-DDDDK-GLP-1 (7-37) (SEQ ID NO: 1) useful for synthesizing liraglutide intermediate polypeptide GLP-1 (7-37), including an amino acid sequence shown in SEQ ID NO. 1, wherein the DDDDK is a linker peptide shown in SEQ ID NO. 2 and the leading peptide shown in SEQ ID NO. 3 is depicted below:

MATKAVSVLKGDGX1VQGIINFEQKESNGX2VKVWGSIKGLX3EGLHGFH
VHKFVNQHLCGX4HLVALX5LV wherein X1 and X2 are each independently any amino acid selected from P and Y;

X3, X4 and X5 are each independently any amino acid selected from S, T and Y.

The invention also provides a recombinant expression vector including a coding gene encoding the fusion protein.

Preferably, the recombinant expression vector is obtained by cloning the coding gene into a plasmid vector pET-28a (+) to obtain a recombinant expression vector pET-28a (+)-Leading Peptide-DDDDK-GLP-1 (7-37).

The invention also provides recombinant engineered bacteria including the recombinant expression vector, which are obtained by transforming the recombinant expression vector pET-28a (+)-Leading Peptide-DDDDK-GLP-1 (7-37) into E. coli strain BL21 (DE3).

The invention also provides use of the recombinant engineered bacteria for the expression of the recombinant liraglutide intermediate GLP-1 (7-37).

The invention also provides a method for synthesizing the liraglutide intermediate polypeptide GLP-1 (7-37) by using the coding gene, which specifically includes the steps of: 1) synthesizing the coding gene encoding the above-mentioned fusion protein of Leading Peptide-DDDDK-GLP-1 (7-37) (SEQ ID NO: 1); 2) ligating the coding gene into an expression vector; 3) transforming the recombinant expression vector carrying the coding gene into E. coli to construct recombinant engineered bacteria; 4) fermenting the recombinant engineered bacteria to induce the expression of the fusion protein in the form of intracellular insoluble inclusion bodies to increase the expression level, wherein the fusion protein includes an amino acid sequence shown in SEQ ID NO. 1; 5) lysing the bacteria, collecting the inclusion bodies, and then washing, denaturing and renaturing the inclusion bodies; and 6) performing enzyme digestion, separation and purification to obtain the intermediate polypeptide GLP-1 (7-37).

As a further improvement of the invention, the coding gene in the step 2) is ligated to the expression vector by inserting into the corresponding cleavage site of the plasmid vector pET-28a (+) via Hind III/Nco I cleavage site.

As a further improvement of the invention, the fermenting of the recombinant engineered bacteria in the step 4) is carried out by high-density fermentation. In a specific method of the high-density fermentation, positive clones of the recombinant engineered bacteria obtained in the step 3) are inoculated into 100 mL LB medium and cultured under shaking at 250 rpm and 37° C. overnight. After that, the bacteria are inoculated into 200 mL LB medium at a ratio of about 0.5-2.0% and cultured under shaking until the $OD_{600}$ value reaches 4-10 to be used as seed inoculum. With 1-5% inoculum size, the seed inoculum is inoculated into 6 L fermentation medium for high-density culturing, wherein the initial fermentation temperature is 37° C., the stirring speed is 200 rpm, the ventilation volume is 40 L/min, and the pH is 6.5-7.3. Then, the stirring speed and ventilation volume are continuously increased to maintain dissolved oxygen at 20% or more consistently. When carbon source is depleted in the starting medium, the dissolved oxygen and pH will rise rapidly, and fed batch fermentation with continuous feed will begin to be performed. When the $OD_{600}$ value of the bacteria reaches 100 or more, IPTG is added to induce for 8 hours, and then the fermentation broth is discharged.

As a further improvement of the present invention, in the step 5), the washed inclusion bodies are added into an inclusion body solubilization buffer under an alkaline condition at a pH of 10-12 at a weight-to-volume ratio of 1:20-1:30, that is at a protein concentration of 20-30 g/L, to perform solubilization, denaturation and renaturation, which reduces the operation volume and the reagent cost. After the solubilization, the inclusion bodies can be directly enzyme digested. The duration of the denaturation and renaturation is no more than 1 h, which allows the process time to be shortened. Moreover, the yield of GLP-1 (7-37) will be improved.

As a further improvement of the invention, specific method of the enzyme digestion, separation and purification in the step 6) is by using enterokinase (1:40 g/U) to enzyme digest the fusion protein after the denaturation and renaturation in the step 5) at 37° C. for 16 to 24 h to obtain a mixed solution including the intermediate polypeptide, tag and linker peptide; and separating the mixed solution by UniSP-50XS cation exchange to obtain the intermediate polypeptide sample with a required purity. The UniSP-50XS cation exchange purification conditions are buffer A: 5-10‰ HAc, pH 3.0-4.0; buffer B: 0.5-2 mol/L NaCl+5-10‰ HAc, pH 4.0-6.0; and buffer C: 25-100 mmol/L PB+0.5-2.0 mol/L NaCl+20-30% IPA, pH 5.0-7.0, wherein the buffer B and the buffer C are used in isocratic purification and elution.

The HPLC purity of the purified liraglutide intermediate polypeptide can achieve 87% or more for side chain modification. The purified polypeptide is identified by HPLC-MASS to have a molecular weight of 3383 Da, which is the right molecular weight of the liraglutide intermediate polypeptide.

The invention has the following advantages over the prior art: (1) the Leading Peptide-DDDDK-GLP-1 (7-37) fusion protein (SEQ ID NO: 1) is constructed by changing a signal peptide of the recombinant sequence, and the expression pattern is changed into the expression of the intracellular insoluble inclusion bodies to increase significantly the expression level; (2) after the washing, the inclusion bodies are solubilized under an alkaline condition by adding into the inclusion body solubilization buffer at the weight-to-volume ratio of 1:20-1:30, that is at the high protein concentration of 20-30 g/L, without the need of a large amount of denaturant. The duration of the denaturation and renaturation is significantly shortened to be no more than 1 h. After the solubilization, the inclusion bodies can be directly enzyme digested, which reduces the process steps, the operation volume and the reagent cost, so as to facilitate the industrialization scale-up; (3) The separation and purification are carried out by the UniSP-50XS cation exchange to obtain a high separation degree, excellent purification effects, a low impurity level and a simple operation. The liraglutide intermediate polypeptide prepared by the invention has a purity up to 87% or more and a yield of more than 85%.

DESCRIPTION OF THE EMBODIMENTS

In order to facilitate those skilled in the art to understand the content of the present invention, the technical solutions of the invention will be further described below in conjunction with the examples, but the following contents should not limit the scope of the invention claimed by the appended claims in any way.

The materials, reagents and the like used in the following examples are commercially available, unless otherwise specified.

Example 1. Construction of Recombinant Engineered Bacteria

Figure 1:
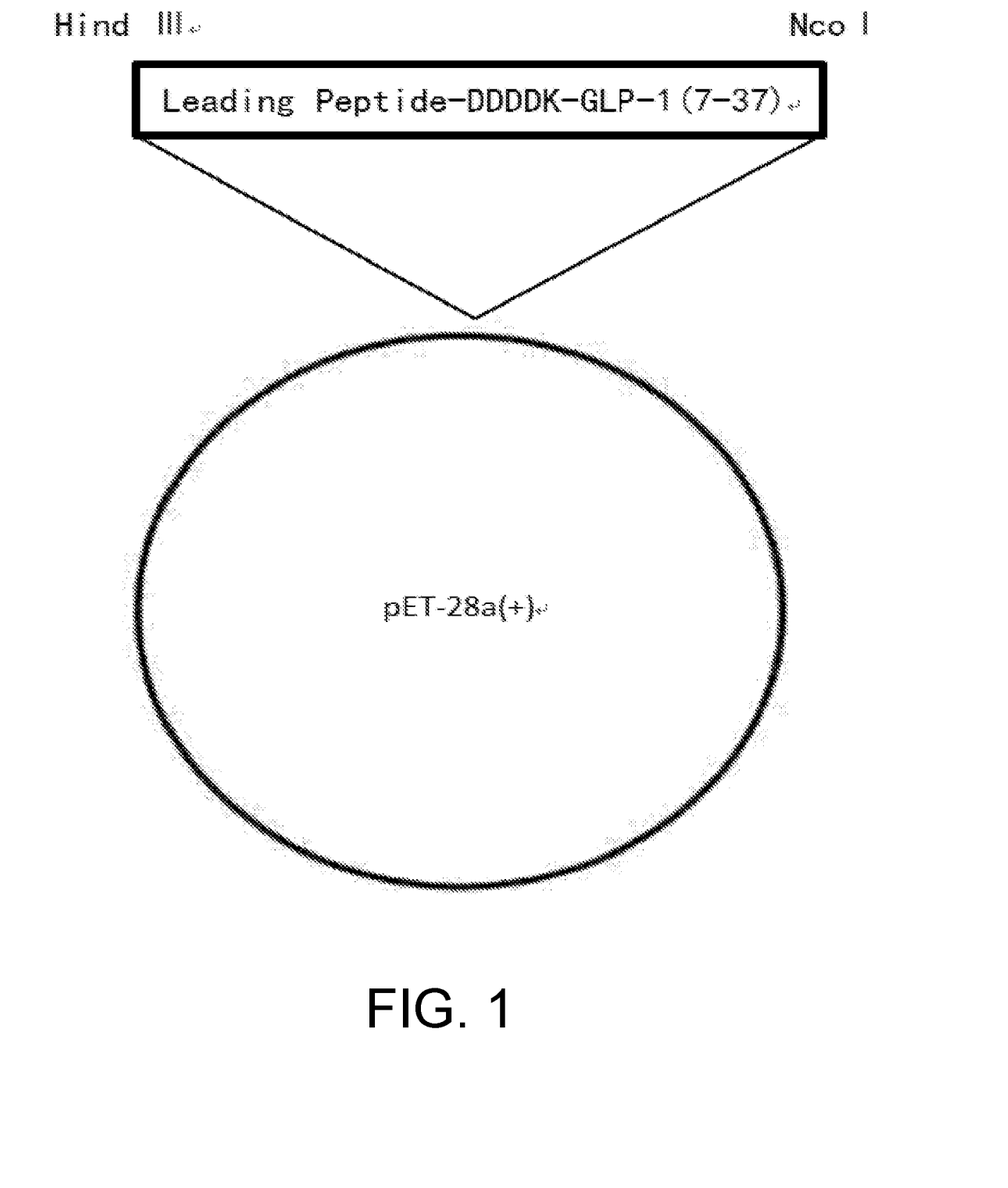
FIG. 1 is a diagram showing the construction of a recombinant plasmid in Example 1.

A gene encoding Leading Peptide-DDDDK-GLP-1 (7-37) fusion protein (SEQ ID NO: 1) was synthesized by a conventional chemical synthetic method, and cDNA of the obtained sequence was inserted into the corresponding cleavage site of plasmid pET-28a (+) via Hind III/Nco I cleavage site. The constructed recombinant plasmid is shown in FIG. 1. The recombinant plasmid, into which the gene encoding the Leading Peptide-DDDDK-GLP-1 (7-37) fusion protein (SEQ ID NO: 1) was inserted, was transformed into host $E.\ coli$ by conventional chemical transformation.

Example 2. High-Density Fermentation

Figure 2:
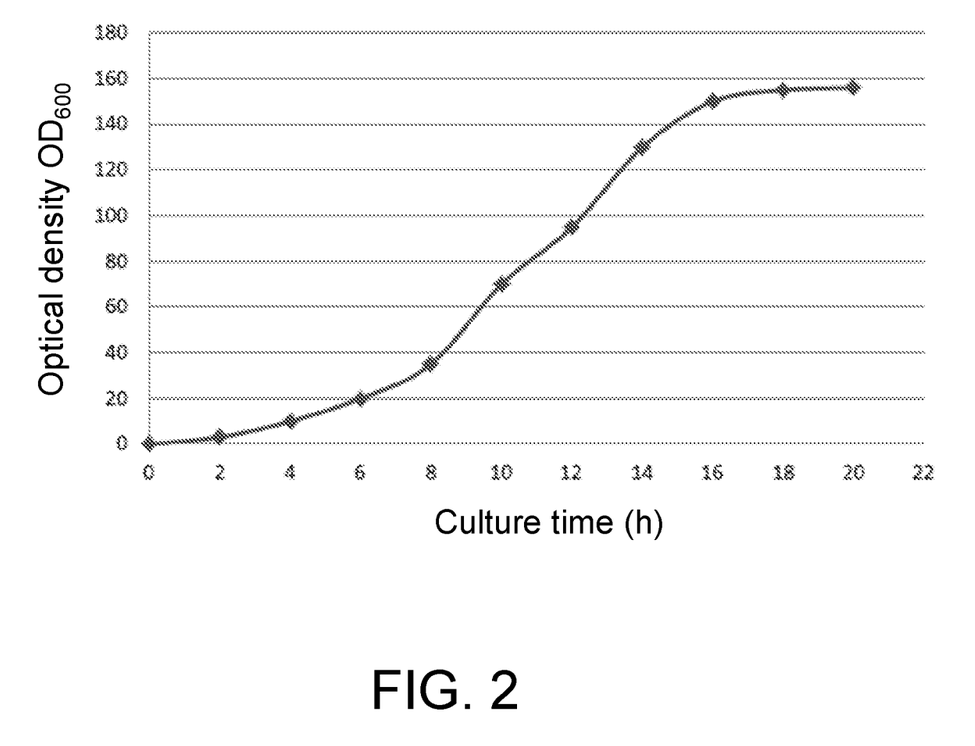
FIG. 2 is a graph showing the growth curve of the bacteria in the fermentation process in Example 2.

The positive clones of the recombinant engineered bacteria obtained in Example 1 were inoculated into 100 mL LB medium and cultured under shaking at 250 rpm and 37° C. overnight. After that, the bacteria were inoculated into 200 mL LB medium at a ratio of 0.5%, and cultured under shaking until $OD_{600}$ value reached 10 to be used as a seed inoculum. The seed inoculum was inoculated into 6 L fermentation medium at 1% inoculum size for high-density culturing. The initial fermentation temperature was 37° C., the stirring speed was 200 rpm, the ventilation volume was 40 L/min, and the pH was 6.5. After that, the stirring speed and the ventilation volume were continuously increased to up to 1000 rpm and 80 L/min, respectively, to maintain the dissolved oxygen at 20% or more consistently, because the high-density fermentation required a large amount of oxygen. If oxygen supply was insufficient, it would not only inhibit the respiration of the bacteria, limiting the growth and reproduction of the bacteria, but also accumulate harmful substances to produce toxic effects on the bacteria, reducing the expression level. When the dissolved oxygen and pH rose rapidly, fed batch fermentation with continuous feed was started. When the $OD_{600}$ value of the fermentation broth exceeded 100, IPTG was added for induction and organic nitrogen source was added, and the fermentation broth was discharged after 8 hours of induction. Then, the bacteria were centrifuged to obtain 213 g/L of the bacteria. The growth curve of the bacteria during fermentation is shown in FIG. 2.

The formulations of the media and pH adjusting agents in this example are as follows:
  LB medium: glucose 10 g/L; yeast 15 g/L; NaCl 10 g/L;
  Fermentation medium: $(NH_4)_2HPO_4$ 4 g/L; $NH_4Cl$ 5 g/L; $KH_2PO_4$ 10 g/L; $MgSO_4.7H_2O$ 5 g/L; citric acid monohydrate 2 g/L; yeast 10 g/L; glucose monohydrate 10 g/L; VB1 trace elements 10 mL/L;
  Feed glucose solution: glucose monohydrate 600 g/L; $MgSO_4$ 25 g/L;
  Organic nitrogen source after induction: yeast 300 g/L;
  pH adjusting agents: phosphoric acid; aqueous ammonia.

Example 3. High-Density Fermentation

The positive clones of the recombinant engineered bacteria obtained in Example 1 were inoculated into 100 mL LB medium and cultured under shaking at 250 rpm and 37° C. overnight. After that, the bacteria were inoculated into 200 mL LB medium at a ratio of 2%, and cultured under shaking until $OD_{600}$ value reached 4 to be used as a seed inoculum. The seed inoculum was inoculated into 6 L fermentation medium at 5% inoculum size for high-density culturing. The initial fermentation temperature was 37° C., the stirring speed was 200 rpm, the ventilation volume was 40 L/min, and the pH was 7.3. After that, the stirring speed and the ventilation volume were continuously increased to up to 1000 rpm and 80 L/min, respectively, to maintain the dissolved oxygen at 20% or more consistently, because the high-density fermentation required a large amount of oxygen. If oxygen supply was insufficient, it would not only inhibit the respiration of the bacteria, limiting the growth and reproduction of the bacteria, but also accumulate harmful substances to produce toxic effects on the bacteria, reducing the expression level. When the dissolved oxygen and pH rose rapidly, fed batch fermentation with continuous feed was started. When the $OD_{600}$ value of the fermentation broth exceeded 100, IPTG was added for induction and organic nitrogen source was added, and the fermentation broth was discharged after 8 hours of induction. Then, the bacteria were centrifuged to obtain 210 g/L of the bacteria.

The formulations of the media and pH adjusting agents in this example were the same as those of Example 2.

Example 4. Purification of Intermediate Polypeptides

Figure 3:
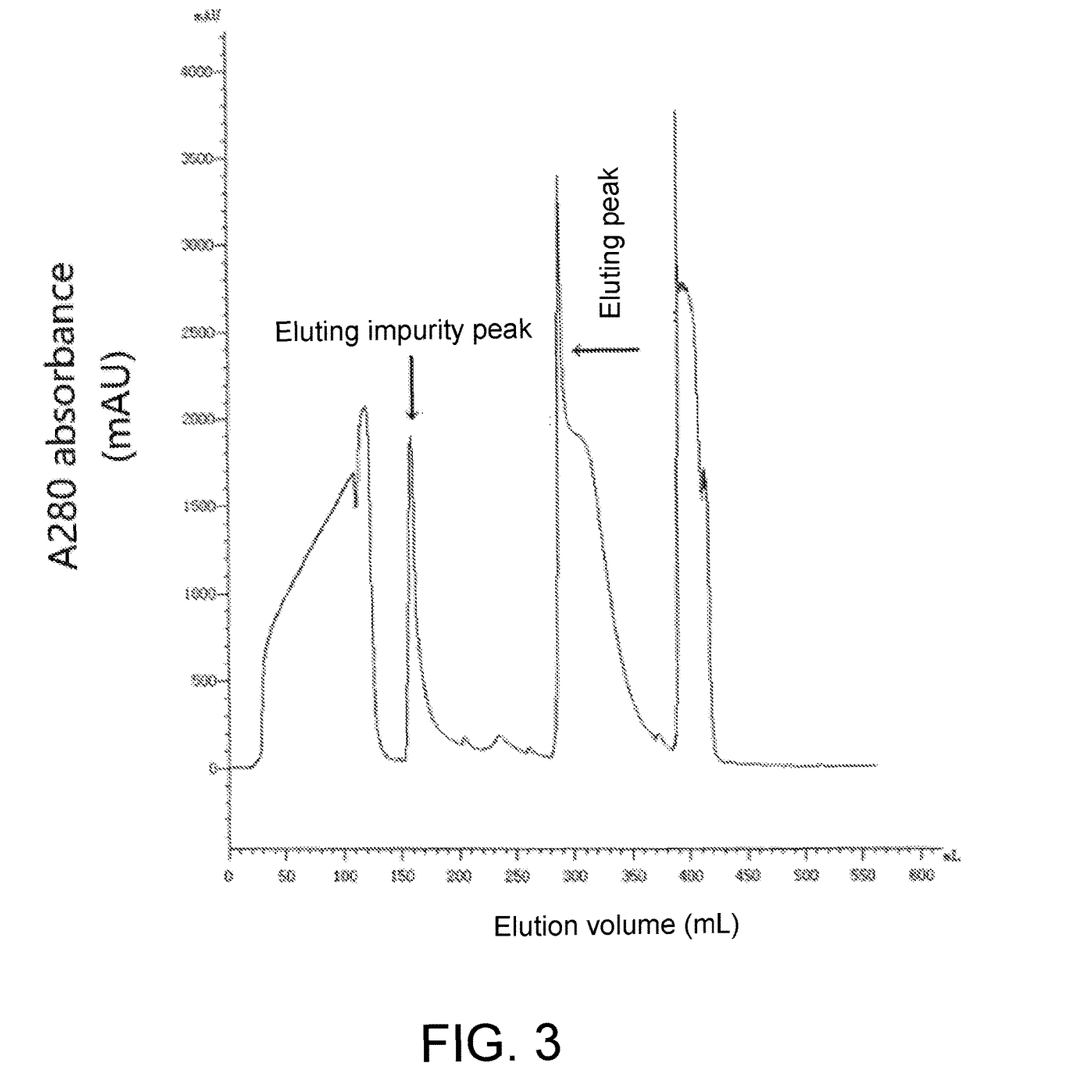
FIG. 3 is a diagram showing the purification of the mixed solution after the enzyme digestion by the UniSP-50XS cation exchange in Example 4.
Figure 4:
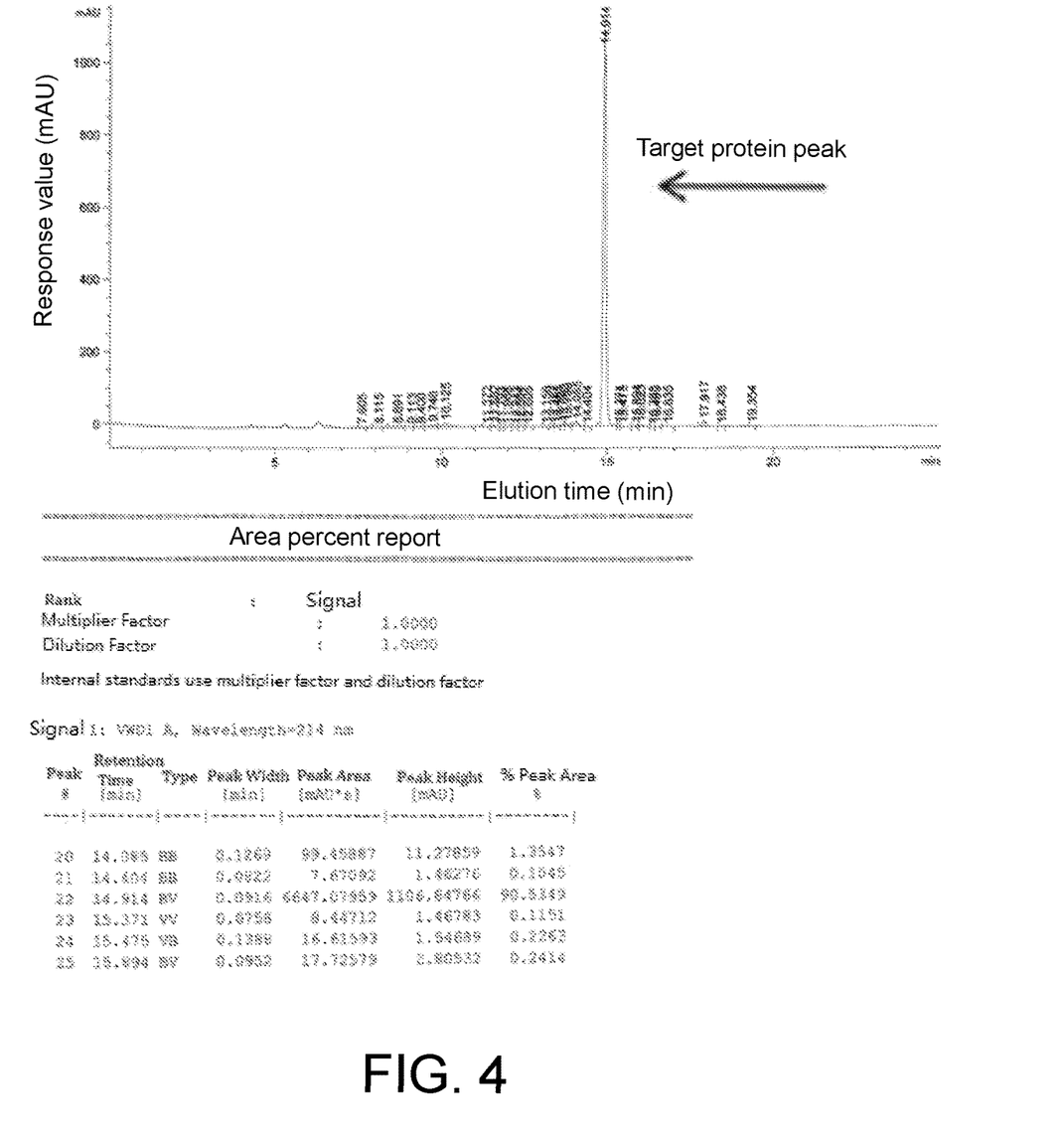
FIG. 4 is an HPLC chromatogram of eluting peaks by the UniSP-50XS cation exchange in Example 4.
Figure 5:
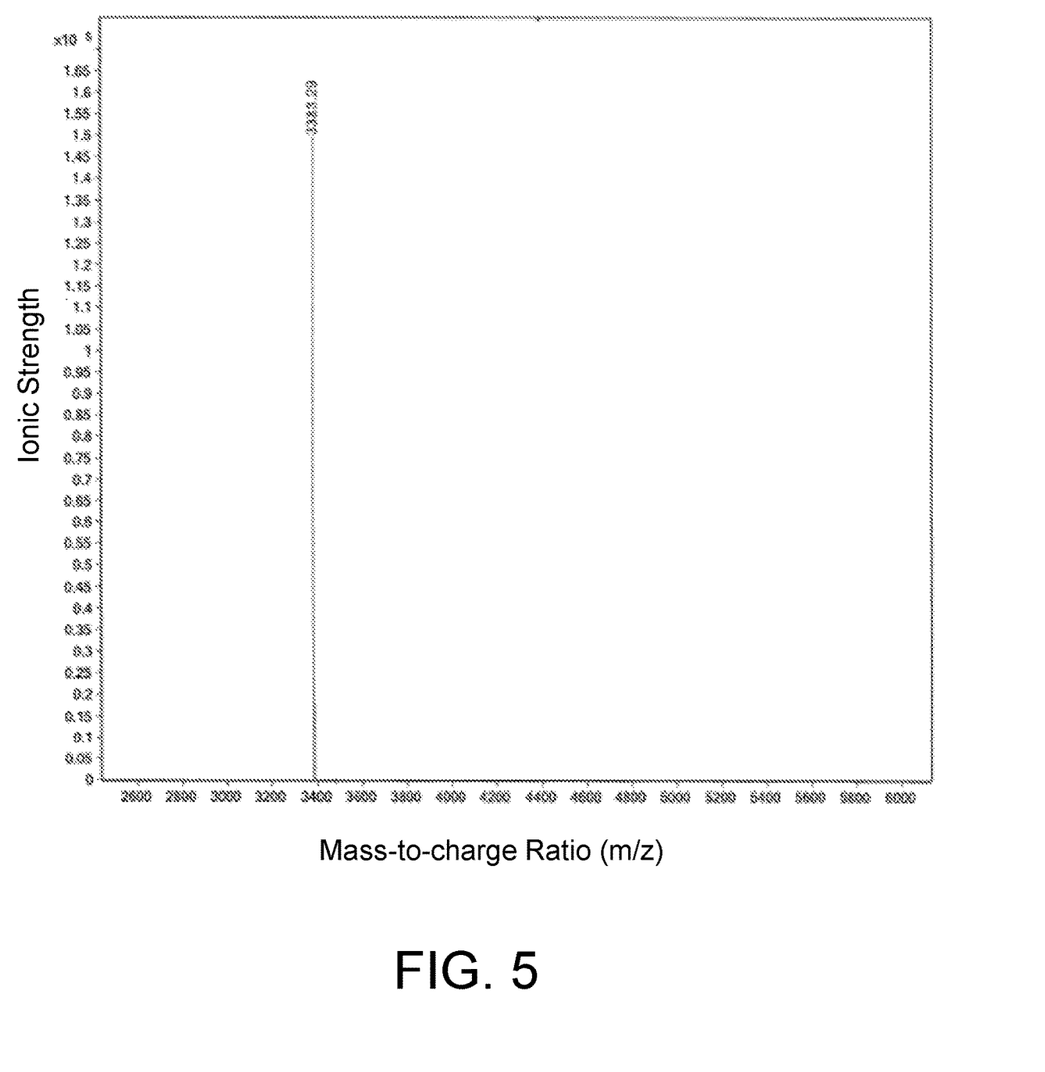
FIG. 5 is a mass spectrum of the intermediate polypeptide in Example 4.

The bacteria were collected from the fermentation broth obtained in Example 2 after the discharge by centrifugation. The collected bacteria were added into a cell lysis buffer at a weight-to-volume ratio of 1:10 and were disrupted twice at the pressure of 900 bar in a high-pressure homogenizer, and then, inclusion bodies were precipitated and collected by centrifugation. The wet weight of the inclusion bodies was 25 g per liter of the fermentation broth. The precipitate was added into a washing buffer at a weight-to-volume ratio of 1:5, stirring at room temperature for 1 h, and the precipitate collected by centrifugation before washing it once with the washing buffer. Then, the washed inclusion bodies were added into an inclusion body solubilization buffer at a weight-to-volume ratio of 1:20 (i.e. at a protein concentration of 20 g/L), and the pH was adjusted to 10.0, and the inclusion bodies were solubilized for 1 h to carry out denaturation and renaturation. After the pH was adjusted to 8.0, the solubilized inclusion bodies were directly added into enterokinase (1:40 g/U) and enzyme digested at 37° C. for 16 h to obtain mixed solution including the intermediate polypeptide, tag and linker peptide. After that, the mixed solution was separated by UniSP-50XS cation exchange to obtain the intermediate polypeptide sample having a purity of 90.5%. The UniSP-50XS cation exchange purification conditions were those in which 1-3 CV of buffer A was used to equilibrate a chromatography column before sample loading; after 0.25 g sample was loaded, 3-8 CV of buffer B was used to wash out impurities and those washed out were eluting impurity peaks; finally, 5-10 CV of buffer C was used to elute, wherein the purity of target peak in the early and the late eluting peaks was not high, and the purity of the target protein peak in the middle eluting peaks was high, as shown in FIG. 3. The eluting peak samples were taken for HPLC and mass spectrometry. The purity of the target protein at the elution time of 14.914 min was detected to be 90.5% by HPLC. The HPLC chromatogram is shown in FIG. 4. The amount of the collected target protein was 0.22 g, and the yield was 88.0%. The molecular weight of the target protein was detected to be 3383.29 Da by mass spectrometry, which was consistent with the molecular weight of the liraglutide polypeptide intermediate, as shown in FIG. 5.

The formulations of the various buffers used in this example are as follows:
Cell lysis buffer: 50 mmol/L Tris+5 mmol/L EDTA, pH 7.0;
Washing buffer: 2 mol/L urea+50 mmol/L Tris+2.0% Triton;
Inclusion body solubilization buffer: 50 mmol/L Tris+10 mmol/L EDTA, pH 12.0;
Buffer A: 5‰ HAc, pH 3.5;
Buffer B: 0.5 mol/L NaCl+5‰ HAc, pH 5.0;
Buffer C: 50 mmol/L PB+1 mol/L NaCl+25% IPA, pH 6.0.

The instrument detection conditions used in this example are as follows:
HPLC conditions: column temperature 40° C.; flow rate 0.5 mL/min; pressure limit 400.0 bar; detection wavelength 214 nm;
Mass spectrometry conditions: ion source voltage 3.5 Kv; Gas Temp 300° C.; Drying Gas 3.0 L/min; Nebulizer 15 psig; collision gas $N_2$; detection mode was positive ion mode.

Example 5. Purification of Intermediate Polypeptides

The bacteria were collected from the fermentation broth obtained in Example 3 after the discharge by centrifugation. The collected bacteria were added into a cell lysis buffer at a weight-to-volume ratio of 1:10 and were disrupted twice at the pressure of 900 bar in a high-pressure homogenizer, and then, inclusion bodies were precipitated and collected by centrifugation. The wet weight of the inclusion bodies was 25 g per liter of the fermentation broth. The precipitate was added into a washing buffer at a weight-to-volume ratio of 1:5, stirring at room temperature for 1 h, and the precipitate collected by centrifugation before washing it once with the washing buffer. Then, the washed inclusion bodies were added into an inclusion body solubilization buffer at a weight-to-volume ratio of 1:30 (i.e. at a protein concentration of 30 g/L), and the pH was adjusted to 12.0, and the inclusion bodies were solubilized for 1 h to carry out denaturation and renaturation. After the pH was adjusted to 9.0, the solubilized inclusion bodies were directly added into enterokinase (1:40 g/U) and enzyme digested at 37° C. for 24 h to obtain mixed solution including the intermediate polypeptide, tag and linker peptide. The UniSP-50XS cation exchange purification conditions were those in which 1-3 CV of buffer A was used to equilibrate a chromatography column before sample loading; after 0.28 g sample was loaded, 3-8 CV of buffer B was used to wash out impurities and those washed out were eluting impurity peaks; finally, 5-10 CV of buffer C was used to elute, wherein the purity of target peak in the early and the late eluting peaks was not high, and the eluting peak was high-purity target protein. The eluting peak samples were taken for HPLC and mass spectrometry. The purity of the target protein was detected to be 87.3% by HPLC and the amount of the collected target protein was 0.24 g. The purification yield was 85.7%. It was detected by mass spectrometry that the molecular weight of the target protein was consistent with the molecular weight of the liraglutide polypeptide intermediate.

The formulations of the various buffers used in this example are as follows:
Cell lysis buffer: 50 mmol/L Tris+5 mmol/L EDTA, pH 7.0;
Washing buffer: 2 mol/L urea+50 mmol/L Tris+2.0% Triton;
Inclusion body solubilization buffer: 40 mmol/L Tris+10 mmol/L EDTA, pH 10.0;
Buffer A: 10‰ HAc, pH 4.0;
Buffer B: 1.0 mol/L NaCl+5‰ HAc, pH 4.5;
Buffer C: 100 mmol/L PB+1.0 mol/L NaCl+30% IPA, pH 6.5.

The instrument detection conditions used in this example were the same as in Example 4.

What is claimed is:

1. A fusion protein, comprising:
Leading Peptide-DDDDK-GLP-1 (7-37) (SEQ ID NO: 1), which is useful for the preparation of a liraglutide intermediate (SEQ ID NO: 4), wherein the DDDDK (SEQ ID NO: 2) is a linker peptide, and the Leading Peptide comprises:
MATKAVSVLKGDGX1VQGIINFEQKESNGX2V-KVWGSIKGLX3E
GLHGFHVHKFVNQHLCGX4HLVALXSLV (SEQ ID NO: 3),
wherein X1 and X2 are each independently any amino acid selected from P and Y; and
X3, X4 and X5 are each independently any amino acid selected from S, T and Y.

2. A recombinant expression vector, comprising a coding gene encoding the fusion protein of claim 1.

3. The recombinant expression vector of claim 2, wherein the recombinant expression vector is pET-28a(+)-Leading Peptide-DDDDK-GLP-1 (7-37) (SEQ ID NO: 1) which is obtained by cloning the coding gene into a plasmid vector pET-28a(+).

4. A recombinant engineered bacteria, comprising the recombinant expression vector of claim 3, wherein the recombinant engineered bacteria are obtained by transforming the recombinant expression vector pET-28a(+)-Leading Peptide-DDDDK-GLP-1 (7-37) (SEQ ID NO: 1) into *E. coli* strain BL21 (DE3).

5. A method for preparing a liraglutide intermediate polypeptide GLP-1 (7-37), comprising the steps of:
1) synthesizing a coding gene which encodes the fusion protein of claim 1;
2) ligating the coding gene into an expression vector to obtain a recombinant expression vector;
3) transforming the recombinant expression vector carrying the coding gene into *E. coli* to construct recombinant engineered bacteria;
4) fermenting the recombinant engineered bacteria to induce expression of the fusion protein in the form of intracellular insoluble inclusion bodies, wherein the fusion protein comprises the amino acid sequence as shown in (SEQ ID NO: 1);
5) lysing the bacteria, collecting the inclusion bodies, and then washing, denaturing and renaturing the inclusion bodies; and
6) performing enzyme digestion, separation and purification to obtain the liraglutide intermediate polypeptide GLP-1 (7-37).

6. The method of claim 5, wherein the coding gene in step 2) is ligated to the expression vector by inserting into a corresponding cleavage site of a plasmid vector pET-28a (+) via a Hind III/Nco I cleavage site.

7. The method of claim 5, wherein the fermenting of the recombinant engineered bacteria in step 4) is carried out by high-density fermentation, and an inducer for inducing the expression of the fusion protein is Isopropylthiogalactoside (IPTG).

8. The method of claim 5, wherein in step 5), the washed inclusion bodies are added into an inclusion body solubilization buffer under an alkaline condition at a pH of 10-12 and at a weight-to-volume ratio of 1:20-1:30, wherein the inclusion bodies are present at a protein concentration of 20-30 g/L, to perform solubilization, denaturation and renaturation for no more than 1 h.

9. The method of claim 5, wherein a specific method of the enzyme digestion, separation and purification in step 6) is by using an enterokinase to digest the fusion protein after the denaturation and renaturation in step 5) for 16-24 h to obtain a mixed solution comprising the liraglutide intermediate polypeptide GLP-1 (7-37), tag and linker peptide; and separating the mixed solution by cation exchange chromatography to obtain the liraglutide intermediate polypeptide GLP-1 (7-37) sample, wherein the cation exchange chromatography conditions are buffer A: 5-10‰ HAc, pH 3.0-4.0; buffer B: 0.5-2 mol/L NaCl+5-10‰ HAc, pH 4.0-6.0; buffer C: 25-100 mmol/L PB+0.5-2.0 mol/L NaCl+20-30% IPA, pH 5.0-7.0.

10. The method of claim 6, wherein the fermenting of the recombinant engineered bacteria in step 4) is carried out by high-density fermentation, and an inducer for inducing the expression of the fusion protein is Isopropylthiogalactoside (IPTG).

11. The method of claim 6, wherein in step 5), the washed inclusion bodies are added into an inclusion body solubilization buffer under an alkaline condition at a pH of 10-12 and at a weight-to-volume ratio of 1:20-1:30, wherein the inclusion bodies are present at a protein concentration of 20-30 g/L, to perform solubilization, denaturation and renaturation for no more than 1 h.

12. The method of claim 6, wherein a specific method of the enzyme digestion, separation and purification in step 6) is by using an enterokinase to digest the fusion protein after the denaturation and renaturation in step 5) in the step 5) for 16-24 h to obtain a mixed solution comprising the liraglutide intermediate polypeptide GLP-1 (7-37), tag and linker peptide; and separating the mixed solution by cation exchange chromatography to obtain the liraglutide intermediate polypeptide GLP-1 (7-37) sample, wherein the cation exchange chromatography conditions are buffer A: 5-10‰ HAc, pH 3.0-4.0; buffer B: 0.5-2 mol/L NaCl+5-10‰ HAc, pH 4.0-6.0; buffer C: 25-100 mmol/L PB+0.5-2.0 mol/L NaCl+20-30% IPA, pH 5.0-7.0.

* * * * *

SEQUENCE LISTING

```
<160> NUMBER OF SEQ ID NOS: 4

<210> SEQ ID NO 1
<211> LENGTH: 103
<212> TYPE: PRT
<213> ORGANISM: Artificial Sequence
<220> FEATURE:
<223> OTHER INFORMATION: Synthesized polypeptide
<220> FEATURE:
<221> NAME/KEY: SIGNAL
<222> LOCATION: (14)..(14)
<223> OTHER INFORMATION: Pro or Tyr
<220> FEATURE:
<221> NAME/KEY: SIGNAL
<222> LOCATION: (29)..(29)
<223> OTHER INFORMATION: Pro or Tyr
<220> FEATURE:
<221> NAME/KEY: SIGNAL
<222> LOCATION: (40)..(40)
<223> OTHER INFORMATION: Ser, Thr or Tyr
<220> FEATURE:
<221> NAME/KEY: SIGNAL
```

```
<222> LOCATION: (59)..(59)
<223> OTHER INFORMATION: Ser, Thr or Tyr
<220> FEATURE:
<221> NAME/KEY: SIGNAL
<222> LOCATION: (65)..(65)
<223> OTHER INFORMATION: Ser, Thr or Tyr

<400> SEQUENCE: 1

Met Ala Thr Lys Ala Val Ser Val Leu Lys Gly Asp Gly Xaa Val Gln
1               5                   10                  15

Gly Ile Ile Asn Phe Glu Gln Lys Glu Ser Asn Gly Xaa Val Lys Val
            20                  25                  30

Trp Gly Ser Ile Lys Gly Leu Xaa Glu Gly Leu His Gly Phe His Val
        35                  40                  45

His Lys Phe Val Asn Gln His Leu Cys Gly Xaa His Leu Val Ala Leu
    50                  55                  60

Xaa Leu Val Asp Asp Asp Lys His Ala Glu Gly Thr Phe Thr Ser
65                  70                  75                  80

Asp Val Ser Ser Tyr Leu Glu Gly Gln Ala Ala Lys Glu Phe Ile Ala
                85                  90                  95

Trp Leu Val Arg Gly Arg Gly
            100

<210> SEQ ID NO 2
<211> LENGTH: 5
<212> TYPE: PRT
<213> ORGANISM: Artificial Sequence
<220> FEATURE:
<223> OTHER INFORMATION: Synthesized linker peptide

<400> SEQUENCE: 2

Asp Asp Asp Asp Lys
1               5

<210> SEQ ID NO 3
<211> LENGTH: 67
<212> TYPE: PRT
<213> ORGANISM: Artificial Sequence
<220> FEATURE:
<223> OTHER INFORMATION: Synthesized leading peptide
<220> FEATURE:
<221> NAME/KEY: SIGNAL
<222> LOCATION: (14)..(14)
<223> OTHER INFORMATION: Pro or Tyr
<220> FEATURE:
<221> NAME/KEY: SIGNAL
<222> LOCATION: (29)..(29)
<223> OTHER INFORMATION: Pro or Tyr
<220> FEATURE:
<221> NAME/KEY: SIGNAL
<222> LOCATION: (40)..(40)
<223> OTHER INFORMATION: Ser, Thr or Tyr
<220> FEATURE:
<221> NAME/KEY: SIGNAL
<222> LOCATION: (59)..(59)
<223> OTHER INFORMATION: Ser, Thr or Tyr
<220> FEATURE:
<221> NAME/KEY: SIGNAL
<222> LOCATION: (65)..(65)
<223> OTHER INFORMATION: Ser, Thr or Tyr

<400> SEQUENCE: 3

Met Ala Thr Lys Ala Val Ser Val Leu Lys Gly Asp Gly Xaa Val Gln
1               5                   10                  15

Gly Ile Ile Asn Phe Glu Gln Lys Glu Ser Asn Gly Xaa Val Lys Val
            20                  25                  30
```

```
Trp Gly Ser Ile Lys Gly Leu Xaa Glu Gly Leu His Gly Phe His Val
            35                  40                  45

His Lys Phe Val Asn Gln His Leu Cys Gly Xaa His Leu Val Ala Leu
 50                  55                  60

Xaa Leu Val
 65

<210> SEQ ID NO 4
<211> LENGTH: 31
<212> TYPE: PRT
<213> ORGANISM: Artificial Sequence
<220> FEATURE:
<223> OTHER INFORMATION: Synthesized liraglutide
<220> FEATURE:
<221> NAME/KEY: PEPTIDE
<222> LOCATION: (20)..(20)
<223> OTHER INFORMATION: N-epsilon-(N-alpha-Palmitoyl-L-gamma-glutamyl)

<400> SEQUENCE: 4

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Arg Gly Arg Gly
            20                  25                  30
```